(12) United States Patent
Zenitani et al.

(10) Patent No.: US 8,518,595 B2
(45) Date of Patent: Aug. 27, 2013

(54) PROTON-CONDUCTING STRUCTURE AND METHOD FOR MANUFACTURING THE SAME

(75) Inventors: Yuji Zenitani, Nara (JP); Takashi Otsuka, Osaka (JP); Tomoko Suzuki, Osaka (JP); Tomoyuki Komori, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/617,793

(22) Filed: Sep. 14, 2012

(65) Prior Publication Data

US 2013/0071766 A1    Mar. 21, 2013

Related U.S. Application Data

(63) Continuation of application No. 13/218,246, filed on Aug. 25, 2011, now Pat. No. 8,298,718, which is a continuation of application No. 12/871,266, filed on Aug. 30, 2010, now Pat. No. 8,029,941, which is a continuation-in-part of application No. PCT/JP2009/006180, filed on Nov. 18, 2009.

(30) Foreign Application Priority Data

Nov. 21, 2008   (JP) ................................. 2008-297541

(51) Int. Cl.
    *H01M 8/10*    (2006.01)
    *H01M 8/00*    (2006.01)

(52) U.S. Cl.
    USPC ............ 429/479; 429/491; 429/535; 429/495

(58) Field of Classification Search
    None
    See application file for complete search history.

(56) References Cited

U.S. PATENT DOCUMENTS

| 8,029,941 B2 | 10/2011 | Zenitani et al. |
| 2005/0221143 A1 | 10/2005 | Kwon et al. |
| 2006/0134507 A1 | 6/2006 | Park et al. |
| 2006/0141316 A1 | 6/2006 | Kang |
| 2007/0166600 A1 | 7/2007 | Kang |
| 2009/0022972 A1 | 1/2009 | Fujita et al. |

FOREIGN PATENT DOCUMENTS

| EP | 2 055 671 A1 | 5/2009 |
| JP | 2005-294245 | 10/2005 |
| JP | 2006-179479 | 7/2006 |
| JP | 2007-188856 | 7/2007 |
| JP | 2008-53225 | 3/2008 |
| WO | WO 2007/083835 A1 | 7/2007 |

OTHER PUBLICATIONS

Non-Final Office Action dated Nov. 25, 2011 for U.S. Appl. No. 13/218,246.

*Primary Examiner* — Barbara Gilliam
*Assistant Examiner* — Angela Martin
(74) *Attorney, Agent, or Firm* — McDermott Will & Emery LLP (57) ABSTRACT

A proton-conducting structure that exhibits favorable proton conductivity in the temperature range of not lower than 100° C., and a method for manufacturing the same are provided. After a pyrophosphate salt containing Sn, Zr, Ti or Si is mixed with phosphoric acid, the mixture is maintained at a temperature of not less than 80° C. and not more than 150° C., and thereafter maintained at a temperature of not less than 200° C. and not more than 400° C. to manufacture a proton-conducting structure. The proton-conducting structure of the present invention has a core made of tin pyrophosphate, and a coating layer formed on the surface of the core, the coating layer containing Sn and O, and having a coordination number of O with respect to Sn of grater than 6.

4 Claims, 7 Drawing Sheets

PROTON-CONDUCTING STRUCTURE AND METHOD FOR MANUFACTURING THE SAME

RELATED APPLICATIONS

This application is a Continuation application of U.S. application Ser. No. 13/218,246, filed on Aug. 25, 2011 now U.S. Pat. No. 8,298,718, which is a Continuation of U.S. application Ser. No. 12/871,266, filed on Aug. 30, 2010, which is now U.S. patent application Ser. No. 8,029,941, which is a continuation-in-part application under U.S.C. 111 (a) of pending prior International application No. PCT/JP2009/006180, filed on Nov. 18, 2009, which in turn claims the benefit of Japanese Application No. 2008-297541 filed on Nov. 21, 2008, the disclosures of which Applications are incorporated by reference herein.

TECHNICAL FIELD

The present invention relates to a proton-conducting structure that contains a pyrophosphate metal salt and is superior in proton conductivity, and a method for manufacturing the same.

BACKGROUND ART

Since a proton conductor conducts only proton, and has electrical properties as an insulator, it has been used as an electrolyte of fuel cells. Among such proton conductors, solid electrolytes composed of a solid polymer (for example, trade name Nafion) or a perovskite type solid oxide have been known, and used for stationary fuel cells, compact and portable fuel cells.

Performance of a proton conductor is evaluated with proton conductivity (Siemens per centimeter: S/cm). The proton conductivity represents the number of conducted protons per unit volume and unit time, and the proton conductivity in the temperature range employed serves as a basis for determining whether or not the proton conductor achieves favorable performance.

Proton conductors composed of a solid polymer currently put into practical applications conduct proton by means of an oxonium ion ($H_3O^+$) in the solid polymer. Thus, since the proton conductivity is exhibited in the state in which water is contained in a large amount in the solid polymer, this solid polymer is used as a solid electrolyte at a temperature not higher than 100° C. at which water evaporation is avoided.

On the other hand, since the proton conductor composed of a perovskite type solid oxide conducts proton by hopping of proton on oxygen constituting the solid oxide, it exhibits proton conductivity at a high temperature of not lower than 600° C. Accordingly, this solid oxide has been used as a solid electrolyte at a temperature of not lower than 600° C. In the proton conductor made of the solid oxide, the proton conductivity increases by setting the temperature in use to a higher temperature, whereas the proton conductivity decreases abruptly when used at lower temperatures.

When the operation temperature of a fuel cell is elevated, reaction efficiency of the catalyst is enhanced, leading to enhancement of efficiency of electric power generation; therefore, a proton conductor which can be used at higher temperatures has been desired. However, polymer solid electrolytes cannot be used at a temperature not lower than 100° C., as described above. On the other hand, there are many restrictions for reliability or durability of a fuel cell system for the operation of the fuel cell at a high temperature of not lower than 600° C. Thus, realization of a proton conductor which can be used in a temperature range of about 100° C. to 400° C. has been desired.

Under such circumstances, investigations of solid electrolytes that exhibit favorable proton conductivity in an intermediate temperature range of not less than 100° C. and not more than 600° C. have been carried out (see, for example, Patent Document 1).

Patent Document 1 discloses that tin pyrophosphate $SnP_2O_7$ is produced by adding phosphoric acid $H_3PO_4$ to tin oxide $SnO_2$ followed by heating, and that thus obtained tin pyrophosphate exhibits high proton conductivity.

PRIOR ART DOCUMENT

Patent Document

Patent Document 1: Japanese Patent Laid-Open Publication No. 2005-294245

SUMMARY OF THE INVENTION

Problems to be Solved by the Invention

However, although tin pyrophosphate was formed in attempts to synthesize tin pyrophosphate according to a method that is similar to the method of Patent Document 1 by the present inventors, the raw material tin oxide remained unreacted, and to yield single-phase tin pyrophosphate was extremely difficult. In addition, when single-phase tin pyrophosphate was synthesized according to a method that is different from the method of Patent Document 1, the proton conductivity was about from $10^{-7}$ S/cm to $10^{-5}$ S/cm, which was not greater than $1/1,000$ as compared with the proton conductivity exhibited by proton conductors which have been put into practical applications. Therefore, the tin pyrophosphate alone exhibited proton conductivity that was insufficient for practical applications, and thus it was deemed that favorable proton conductivity was not able to be realized.

From the foregoing, an object of the present invention is to provide a proton-conducting structure that exhibits favorable proton conductivity in the temperature range of not lower than 100° C., and a method for manufacturing the same.

Means for Solving the Problems

The present inventors obtained the following findings as a result of investigations elaborately carried out with respect to a proton conductor that exhibits favorable proton conductivity in the temperature range of not lower than 100° C.

(i) A structure that exhibits extremely favorable proton conductivity in an intermediate temperature range can be obtained by mixing a pyrophosphate metal salt such as tin pyrophosphate with phosphoric acid, followed by subjecting the mixture to a two-step heat treatment under certain conditions.

(ii) The structure manufactured using tin pyrophosphate has a core of the tin pyrophosphate inside thereof, and at least a part of the surface of the core is covered by a layer containing Sn and P, the layer having a coordination number of O with respect to Sn of grater than 6.

From the findings described above, the present invention was accomplished.

More specifically, the present invention relates to a method for manufacturing a proton-conducting structure comprising: a first heat treatment step of subjecting a mixture containing a pyrophosphate salt containing at least one metal element selected from the group consisting of Sn, Zr, Ti and Si, and phosphoric acid to a heat treatment at a predetermined temperature in the range of not less than 80° C. and not more than 150° C.; and a second heat treatment step of subjecting the mixture, which has been treated with heat in the first heat treatment step, to a heat treatment at a predetermined temperature in the range of not less than 200° C. and not more than 400° C.

Furthermore, the present invention also relates to a proton-conducting structure comprising a core made of tin pyrophosphate, and a coating layer formed on at least a part of the surface of the core, the coating layer containing Sn and O, and having a coordination number of O with respect to Sn of grater than 6.

Moreover, the present invention also relates to a method for generating an electric power comprising the step of allowing proton to be conducted to permit electric power generation with a fuel cell comprising: an electrolyte having a core made of tin pyrophosphate, and a coating layer formed on at least a part of the surface of the core, the coating layer containing Sn and O, and having a coordination number of O with respect to Sn of grater than 6; and a pair of electrodes attached to the surface of the coating layer.

Effects of the Invention

According to the present invention, a proton-conducting structure that exhibits proton conductivity providing significantly superior performance over single-phase tin pyrophosphate in an intermediate temperature range of not lower than 100° C. can be obtained. Thus, a practically applicable proton-conducting structure that exhibits favorable proton conductivity in an intermediate temperature range of not lower than 100° C. at which conventional proton conductors were not able to be used can be realized.

MODE FOR CARRYING OUT THE INVENTION

Hereinafter, an embodiment of the present invention will be described with reference to drawings.
(Embodiment)
FIG. 1 shows a conceptual diagram of a construction of a proton-conducting structure according to an embodiment of the present invention.

Figure 1:
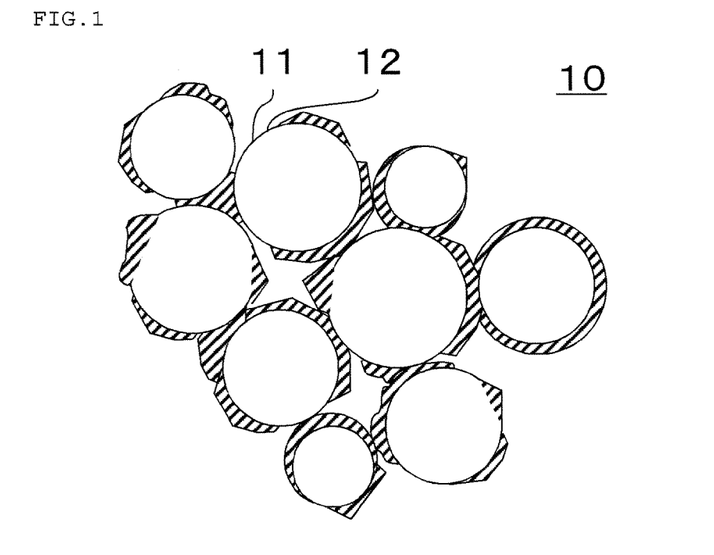
FIG. 1 shows a conceptual diagram illustrating a construction of a proton-conducting structure according to an embodiment of the present invention.

As shown in FIG. 1, with regard to a proton-conducting structure 10 that is a solid electrolyte, the surface of a core 11 made of tin pyrophosphate is covered with a coating layer 12 containing Sn and O. The coating layer 12 may cover the entire surface of the core 11. Alternatively, as shown in FIG. 1, the coating layer 12 may cover only a part of the surface of the core 11. Namely, the surface of the core may have a region not covered by the coating layer.

The shape and the size of the core 11 made of tin pyrophosphate are not particularly limited. However, in order to increase the contact area with proton to achieve favorable proton conductivity, the core 11 is preferably powdery.

The coating layer 12 in the present invention contains Sn and O as constitutive elements. Additionally, in the coating layer 12, the coordination number of O with respect to Sn (number of O atoms per one Sn atom) is greater than 6. The coordination number of O with respect to Sn can be readily determined by measuring the structure according to an X-ray absorption spectroscopic method, particularly a conversion particle yield process. According to this procedure, the coordination number can be observed from the sample surface to the interior with a depth of about 100 nm.

The tin pyrophosphate has a theoretical coordination number of O with respect to Sn of 6, whereas the found value is less than 6. From this result, it is concluded that the coating layer 12 made of a material containing Sn and O other than tin pyrophosphate is formed on the surface of the core 11 made of tin pyrophosphate in the proton-conducting structure of the present invention.

Although details of the material that may form the coating layer 12 are unknown, the material is believed to contain tin oxide since a high coordination number of O with respect to Sn is exhibited. Although phosphoric acid is used for forming the coating layer 12 as described later, phosphoric acid will be almost sputtered since a heat treatment step is conducted at a high temperature in the formation. Thus, in the coating layer 12, phosphoric acid is not contained as a principal constitutive element. However, a slight amount of phosphoric acid may be contained. Since the constituent material of the coating layer cannot be observed with the X-ray diffraction as described later, it is believed that the coating layer does not have a crystal structure but is in an amorphous state.

Since a theoretical maximum coordination number of O with respect to Sn is 12, the coordination number of O with respect to Sn exhibited by the coating layer 12 is less than 12. In order to achieve more superior proton conductivity, the coordination number of O with respect to Sn exhibited by the coating layer 12 preferably falls within the range of 7 to 8.5.

The thickness of the coating layer 12 is not particularly limited, and may vary greatly depending on the place as shown in FIG. 1, but is typically not less than 0 to about several hundred nm.

The proton-conducting structure of the present invention is a solid electrolyte. When the core 11 is powdery, the proton-conducting structure of the present invention is preferably molded into a predetermined shape such as, for example, pellet or sheet in order to facilitate the handling.

Figure 2:
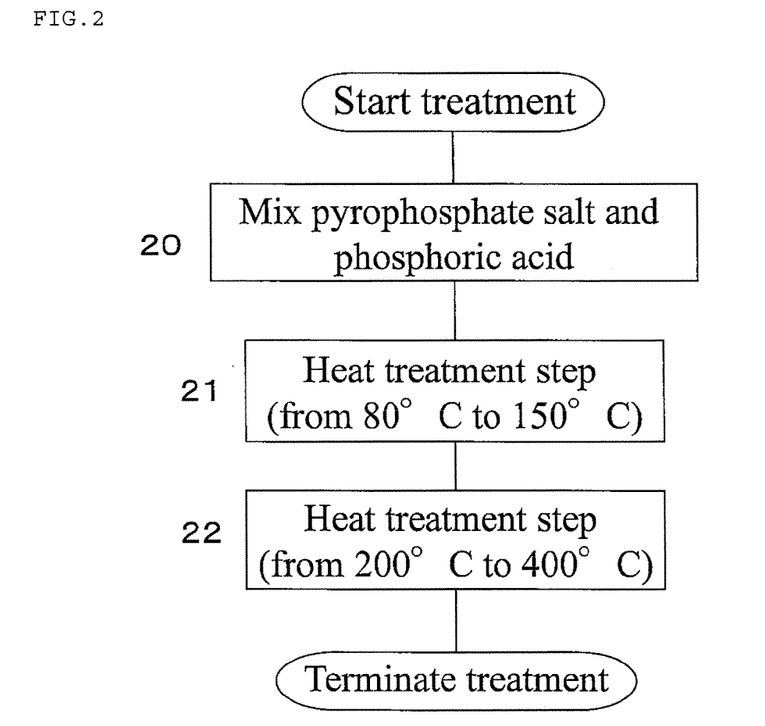
FIG. 2 shows a flow chart illustrating a method for manufacturing the proton-conducting structure according to an embodiment of the present invention.

FIG. 2 shows a flow chart illustrating a method for manufacturing a proton-conducting structure in an embodiment of the present invention.

According to the present invention, the proton-conducting structure can be prepared by, for example, the method as shown in FIG. 2. As a raw material, a pyrophosphate salt containing at least one metal element selected from the group consisting of Sn, Zr, Ti and Si, i.e., at least one selected from the group consisting of tin pyrophosphate, zirconium pyrophosphate, titanium pyrophosphate and silicon pyrophosphate can be used. When tin pyrophosphate is used, the proton-conducting structure of the present invention described above can be obtained. When any one of zirconium pyrophosphate, titanium pyrophosphate and silicon pyrophosphate is used, the resulting proton-conducting structure is believed to have a structure similar to the structure of the proton-conducting structure of the present invention. In other words, it is believed that a proton-conducting structure is formed which comprises a core made of any one of zirconium pyrophosphate, titanium pyrophosphate and silicon pyrophosphate, and a coating layer formed on at least a part of the surface of the core, the coating layer containing O and any one of Zr, Ti and Si. It is to be noted that the coating layer is formed depending on the substance of the aforementioned core; therefore, when the core is made of zirconium pyrophosphate, for example, the coating layer will contain Zr and O. Alternatively, the aforementioned core may contain not only any one of zirconium pyrophosphate, titanium pyrophosphate and silicon pyrophosphate, but arbitrary two of the three substances, or all the three substances may be contained. In addition, the aforementioned coating layer may contain not only one of Zr, Ti and Si depending on the type of the material of the aforementioned core, but arbitrary two of the three substances, or all the three substances may be contained.

Hereinafter, the manufacturing method of the present invention will be specifically explained.

First, in a treatment step 20, the aforementioned pyrophosphate metal salt, preferably the powder thereof is mixed with phosphoric acid ($H_3PO_4$). As the phosphoric acid, either a pure form or an aqueous solution may be used. Although the conditions in mixing are not particularly limited, it is preferred to stir sufficiently after both components are combined such that the surface of the pyrophosphate metal salt is evenly brought into contact with phosphoric acid. The ratio of the phosphoric acid to the pyrophosphate metal salt used is not particularly limited. The ratio can be adjusted appropriately depending on the surface area of the pyrophosphate metal salt. However, when the amount of the phosphoric acid used is too small, the amount of formation of the coating layer becomes so low that sufficient proton conductivity cannot be secured. Therefore, it is preferred that the molar ratio of phosphorus in the phosphoric acid relative to the metal (Sn, Zr, Ti, Si) in the pyrophosphate metal salt is approximately 0.1 to 0.7.

Although the pyrophosphate metal salt having a variety of shapes may be used, when the powder thereof is used, the particle size may be on a micron order such as, for example about 0.1 to 10 micron.

When the pyrophosphate metal salt is a powder, the mixture obtained in the treatment step 20 may be molded into a predetermined shape such as pellet or sheet using a general mold processing machine. The molding in this stage is preferred since it can be easily carried out. The molded mixture is subjected to a treatment in the following heat treatment step 21.

The mixture obtained in the treatment step 20 is subjected to a heat treatment by maintaining under temperature conditions of not less than 80° C. and not more than 150° C. in the heat treatment step 21. In this step, the heating temperature may fall within the range of not less than 80° C. and not more than 150° C., and may be maintained constant within this range. Alternatively, the temperature may be altered continuously or stepwise within this range. The time period of the heat treatment carried out may be adjusted appropriately, but for example, the treatment may be carried out for about 10 min or longer, and preferably for about 1 hour.

The mixture subjected to the heat treatment in the heat treatment step 21 is subjected to a treatment in the following heat treatment step 22. In this step, the aforementioned mixture is subjected to a heat treatment under temperature conditions of not less than 200° C. and not more than 400° C. Accordingly, a structure that exhibits favorable proton conductivity can be obtained. The heating temperature in this step may fall within the range of not less than 200° C. and not more than 400° C., and may be maintained constant within this range. Alternatively, the temperature may be altered continuously or stepwise within this range. The time period of the heat treatment carried out may be adjusted appropriately, but for example, the treatment may be carried out for about 10 min or longer, and preferably for about 1 hour.

According to the two-step heat treatment in the foregoing, a structure that exhibits favorable proton conductivity is obtained. Since it was demonstrated that some sort of reaction processes proceed sequentially in the temperature range of not less than 80° C. and not more than 150° C., and in the temperature range of not lower than 200° C. as described later, it is inferred that a sort of reactions caused between the surface of the pyrophosphate metal salt and phosphoric acid leads to formation of a coating layer containing a metal (Sn, Zr, Ti, Si) and O on the surface, and this coating layer promotes conduction of proton.

It is to be noted that when tin oxide or a simple oxide such as silica or alumina is used in place of the pyrophosphate metal salt as a raw material in the manufacturing method of the present invention, a structure that exhibits favorable proton conductivity cannot be obtained.

The proton-conducting structure of the present invention may be used as an electrolyte in a fuel cell. The fuel cell is constructed to comprise the electrolyte, and a pair of electrodes disposed to be in contact with the aforementioned coating layer. This fuel cell executes electric power generation by conducting proton via the electrolyte.

Figure 10:
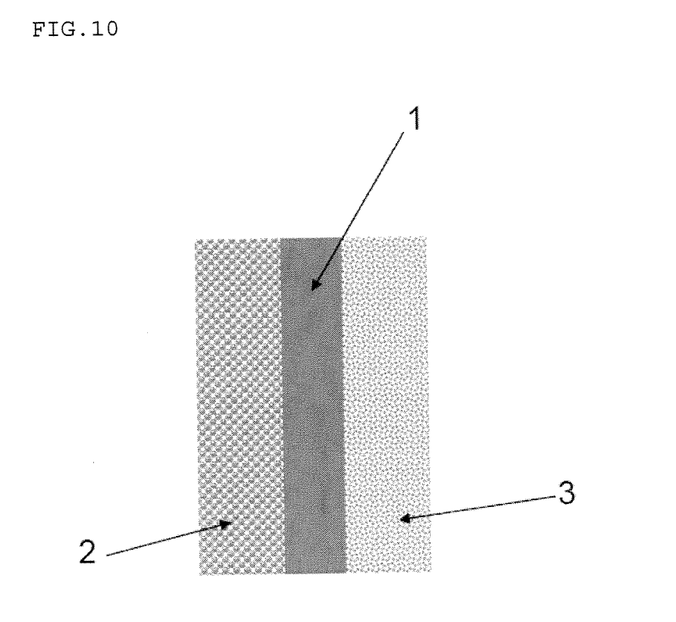
FIG. 10 shows a fuel cell comprising a solid electrolyte membrane 1 composed of the proton-conducting structure of the present invention, a cathode 3, and an anode 2.

Specifically, as shown in FIG. 10, a fuel cell comprises a solid electrolyte membrane composed of the proton-conducting structure 1 of the present invention, a cathode 3, and an anode 2. Oxygen and Hydrogen are supplied respectively to the cathode 3 and the anode 2 to generate an electric power. Needless to say, the cathode 3 and the anode 2 interpose the solid electrolyte membrane.

Figure 11:
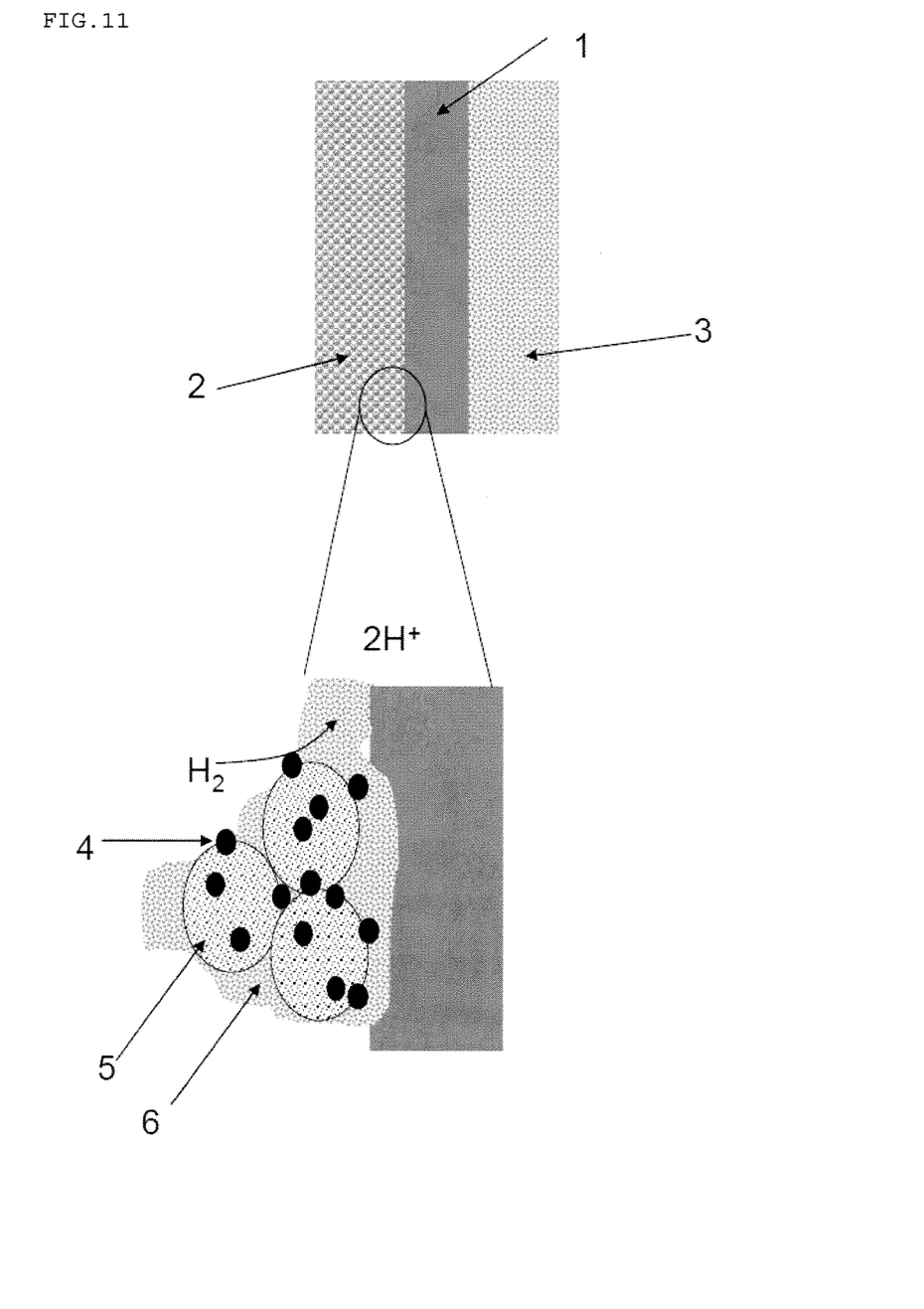
FIG. 11 shows a fuel cell in which the proton-conducting structure of the present invention is used as an electrolyte coating a catalyst-holding particle 5 in a cathode 3 and an anode 2.

As shown in FIG. 11, the proton-conducting structure may be used as an electrolyte coating a catalyst-holding particle in a cathode 3 and an anode 2. Specifically, a fuel cell comprising a solid electrolyte membrane 1, a cathode 3, and an anode 2 is prepared. At least either of the cathode 3 and the anode 2 comprises a catalyst-holding particle 5 coated with the electrolyte composed of the proton-conducting structure 6 of the present invention. The solid electrolyte membrane 1 is not limited. However, it may be composed of the proton-conducting structure of the present invention. Oxygen and Hydrogen are supplied respectively to the cathode 3 and the anode 2 to generate an electric power. It is preferred that the catalyst-holding particle 5 is composed of a carbon particle holding a catalyst 4 such as platinum on its surface.

EXAMPLES

Hereinafter, the present invention will be explained in more detail by way of Examples, and the present invention is not limited to these Example. The process for production may be carried out with any appropriate modification as long as the spirit of the present invention is not altered.

Example 1

The proton-conducting structure of the present invention was manufactured according to the following method.

Powdery (about 1 μm) tin pyrophosphate (manufactured by Nippon Chemical Industrial Co., Ltd.) in an amount of 0.9807 g, and $H_3PO_4$ (manufactured by Wako Pure Chemical Industries, Ltd., a conc. phosphoric acid aqueous solution of 85% concentration) in an amount of 0.1931 g were weighed such that the molar ratio of Sn:P became 1:0.5. Then, both components were placed into an agate mortar, and mixed by stirring for 30 min.

Thus obtained mixture was filled into a die, and molded to a pellet form using a uniaxial press molding machine at a pressure of 100 kg/cm$^2$.

The molded mixture was maintained while heating in an electric furnace at a temperature of 120° C. for 1 hour (heat treatment step 21), and then maintained while heating at a temperature of 400° C. for 1 hour (heat treatment step 22). Accordingly, a proton-conducting structure was prepared.

(Structure Evaluation)

The coordination number of O with respect to Sn in the vicinity of the surface of the proton-conducting structure obtained in Example 1 was determined according to the following procedure.

The coordination number of O with respect to Sn in the vicinity of the surface of the proton-conducting structure was measured according to a conversion particle yield process that enables the coordination number of O with respect to Sn to be observed from the surface of the sample to the depth of about 100 nm. Specifically, using a conversion particle yield process that is one procedure of X-ray absorption spectroscopic methods, an X-ray absorption spectroscopic value in the range of from 4,290 eV to 5,400 eV involving 4,467 eV that represents the energy at an SnL1-shell absorption edge was measured to observe the coordination number. As a result, the coordination number of O with respect to Sn was 8.5. Thus, it was ascertained that the coordination number of O with respect to Sn was grater than 6 in the vicinity of the surface of the proton-conducting structure.

Using a similar procedure, tin pyrophosphate (manufactured by Nippon Chemical Industrial Co., Ltd.) as a raw material was subjected to the measurement, and as a result, the coordination number of O with respect to Sn being 5.2 was demonstrated. It is to be noted that tin pyrophosphate usually has an octahedral structure of $SnO_6$, and the coordination number of O with respect to Sn is theoretically 6. The above found value is believed to be lower than the theoretical value due to oxygen deficiency in the vicinity of the surface.

From the foregoing, it was verified that a layer made of a material that is different from tin pyrophosphate was formed with the coordination number of O with respect to Sn being more than 6, in the vicinity of the surface of the proton-conducting structure of the present invention.

Figure 3:
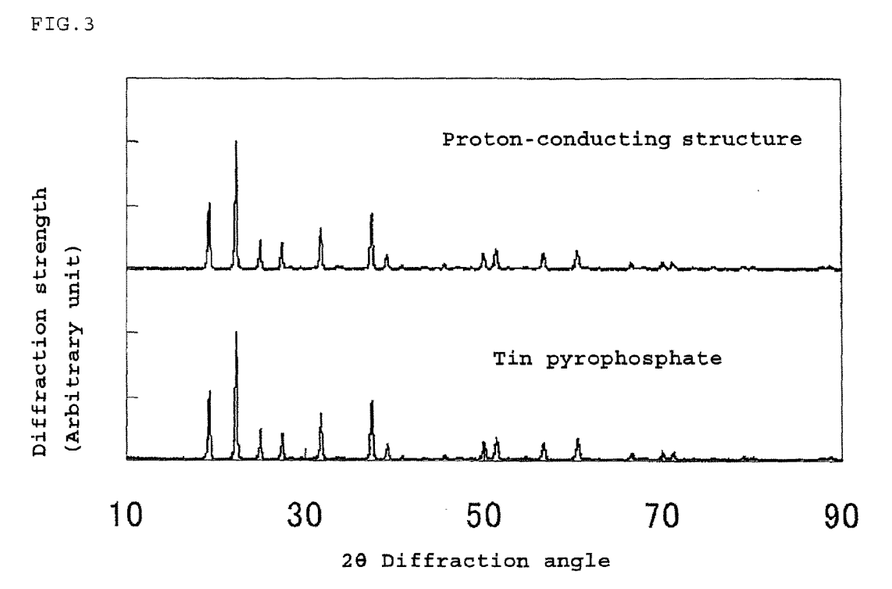
FIG. 3 shows a view illustrating results of measurement of X-ray diffraction on the proton-conducting structure of the present invention, and on tin pyrophosphate.

In order to confirm as to whether or not the structure was altered after tin pyrophosphate used as the raw material of the proton-conducting structure of the present invention was subjected to the heat treatment step 21 and the heat treatment step 22, measurement of an X-ray diffraction was carried out on both the proton-conducting structure of the present invention and tin pyrophosphate. FIG. 3 shows the results. In FIG. 3, the upper chart shows the result of the measurement on the proton-conducting structure of the present invention, whereas the lower chart shows the result of the measurement on the tin pyrophosphate. FIG. 3 suggests that both components gave equivalent diffraction peaks in the range of the diffraction angle of from 10° to 90°. Accordingly, it was ascertained that the proton-conducting structure of the present invention retained the identical crystal structure to that of tin pyrophosphate.

From the results of the measurement with the X-ray absorption spectroscopic method according to the above conversion particle yield process, and the measurement of an X-ray diffraction, it was proven that the proton-conducting structure of the present invention had as the core 11 tin pyrophosphate having a crystal structure retained, and on at least a part of the surface of the core 11 the coating layer 12 formed having an amorphous structure, in which the coating layer 12 had a coordination number of O with respect to Sn of greater than 6, and was made of a material that is different from tin pyrophosphate.

(Evaluation of Proton Conductivity)

Evaluation of proton conductivity on the proton-conducting structure obtained in Example 1 was made using a four-terminal conductivity measurement apparatus by measuring the impedance. An electrode was formed directly on the surface of the structure by allowing for vapor deposition of platinum and palladium on the front face and the back face of the proton-conducting structure in the pellet form. After a gold wire was adhered on the formed electrode using a silver paste, the measurement was carried out under an experimental condition of the measuring frequency of from 0.1 Hz to 10 MHz, and a voltage magnitude of 2 V, in a temperature range of from the room temperature to 250° C.

Figure 4:
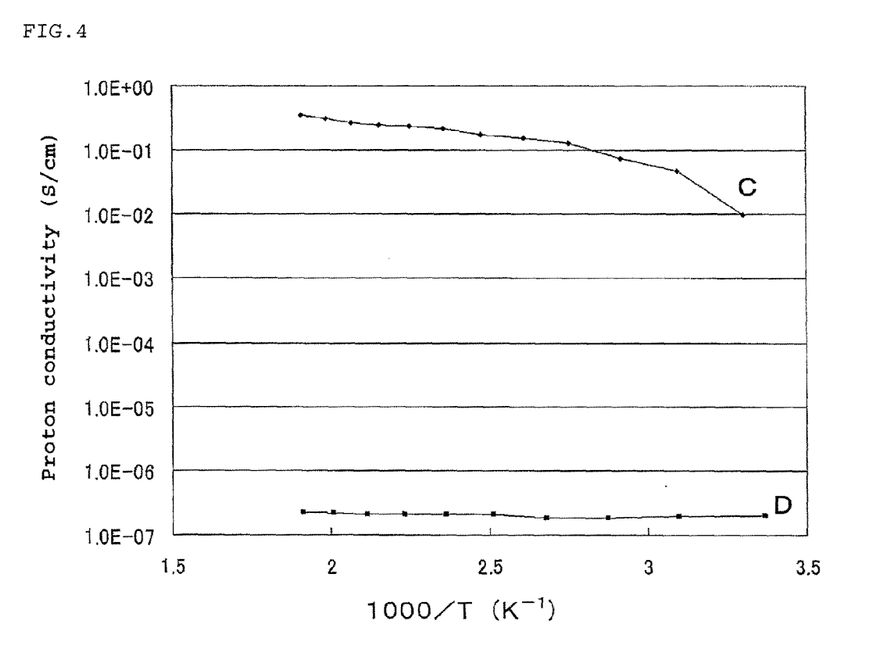
FIG. 4 shows a view illustrating results of measurement of the proton conductivity in the proton-conducting structure of the present invention, and in tin pyrophosphate.

FIG. 4 shows the results of the temperature dependency of the resulting proton conductivity. In FIG. 4, "C" indicates the measurement results on the proton-conducting structure of Example 1, whereas "D" indicates the measurement results under the same condition on the tin pyrophosphate molded into a pellet form. It should be noted that the horizontal axis in FIG. 4 represents values derived by converting the measurement temperature to a Kelvin unit, and then multiplying its reciprocal number by 1,000. From these results, it was verified that the proton-conducting structure of the present invention exhibited significantly higher proton conductivity as compared with tin pyrophosphate in the temperature range of from the room temperature to 250° C.

From the foregoing results, significant improvement of the proton conductivity was ascertained as compared with tin pyrophosphate, according to the proton-conducting structure having tin pyrophosphate as the core 11, which had a coating layer 12 formed on at least a part of the surface thereof, the coating layer 12 having a coordination number of O with respect to Sn of greater than 6.

In order to confirm the reproducibility of the aforementioned experiment, similar procedure was used to manufacture a proton-conducting structure, and the measurement of the proton conductivity was similarly carried out. As a result, the proton conductivity was 0.15 S/cm at a measurement temperature of 100° C., and 0.23 S/cm at a measurement temperature of 200° C.

From the foregoing results, it was proven that the proton-conducting structure of the present invention had superior proton conductivity and high reproducibility in the temperature range of not lower than 100° C.

(Analysis of Reaction Steps)

In order to clarify the conditions for manufacturing the proton-conducting structure of the present invention, a differential thermal analysis (DTA measurement) was carried out.

Figure 5:
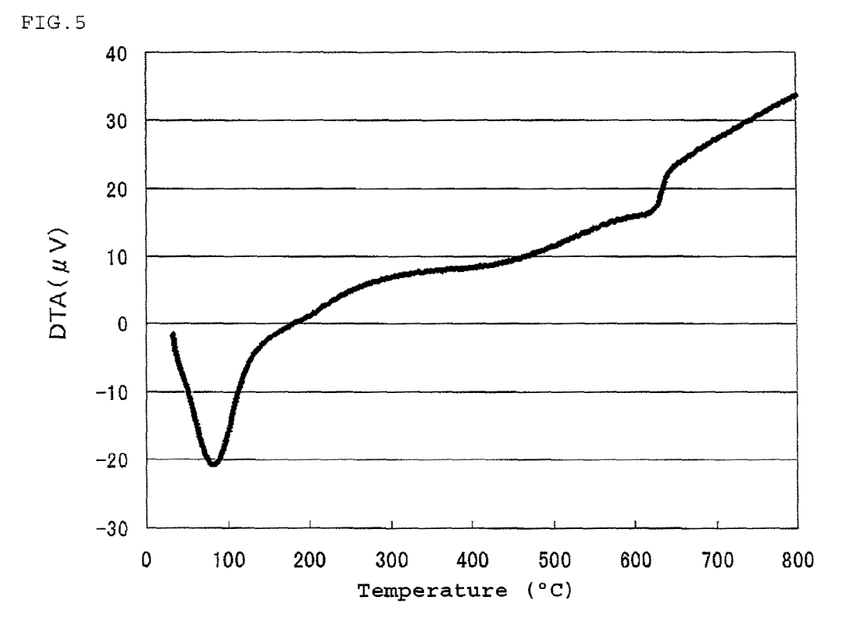
FIG. 5 shows a view illustrating results of measurement of DTA on the mixture of raw materials of the present invention.

FIG. 5 shows the results of the DTA measurement carried out using a mixture of tin pyrophosphate and $H_3PO_4$.

Powdery (about 1 μm) tin pyrophosphate (manufactured by Nippon Chemical Industrial Co., Ltd.) and $H_3PO_4$ (manufactured by Wako Pure Chemical Industries, Ltd., a conc. phosphoric acid aqueous solution of 85% concentration) were mixed such that the molar ratio of Sn:P became 1:0.5 to produce the mixture described above. In order to adjust to the aforementioned molar ratio, 0.9807 g of tin pyrophosphate, and 0.1931 g of $H_3PO_4$ were weighed. Both components were placed into an agate mortar, and mixed by stirring for 30 min. With respect to thus obtained mixture, the DTA measurement was carried out by rising the temperature from the room temperature to 800° C. at a constant rate.

The results reveal that an endothermic reaction proceeded in the temperature range of lower than 80° C. The progress of this endothermic reaction results from evaporation of water which had been contained in the conc. phosphoric acid aqueous solution. In addition, it is revealed that an exothermic reaction proceeded at a temperature of not lower than 80° C. since the differential thermocouple voltage value increased. Namely, it is believed that a sort of a synthetic reaction caused in this temperature range.

Figure 6:
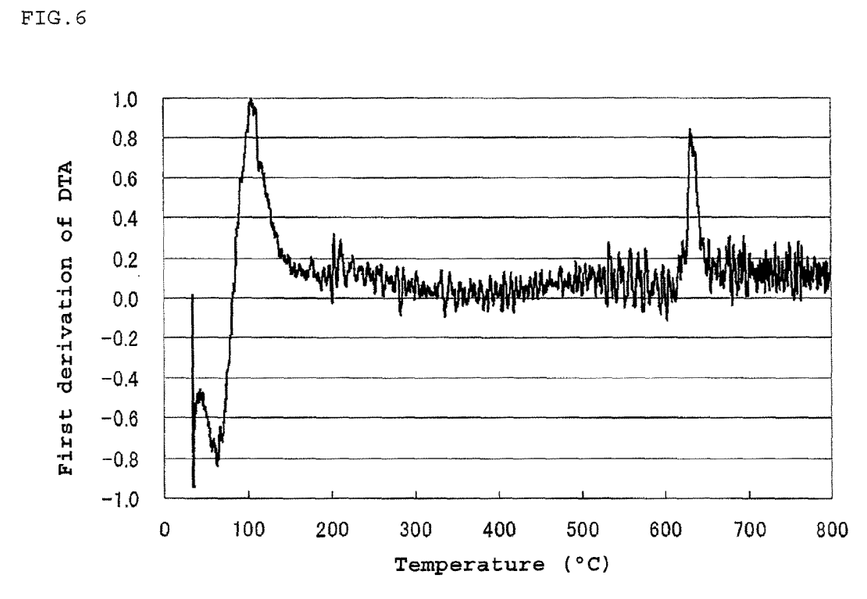
FIG. 6 shows a view illustrating first derivation of results of measurement of DTA on the mixture of the raw materials of the present invention.

FIG. 6 shows results of first derivation of the results of the DTA measurement shown in FIG. 5.

As is shown in FIG. 6, peaks were present in the range of from 80° C. to 150° C., and additional peaks are present at 200° C. and 630° C. in the still higher temperature range. From these results, it is revealed that the synthetic reaction proceeded in the range of from 80° C. to 150° C., whereas another synthetic reaction starts again at 200° C.

From the foregoing results, it is proven that there are two kinds of synthetic reaction processes in the temperature range of from 80° C. to 150° C., and the temperature range of not lower than 200° C., according to the method for manufacturing the proton-conducting structure of the present invention.

Figure 7:
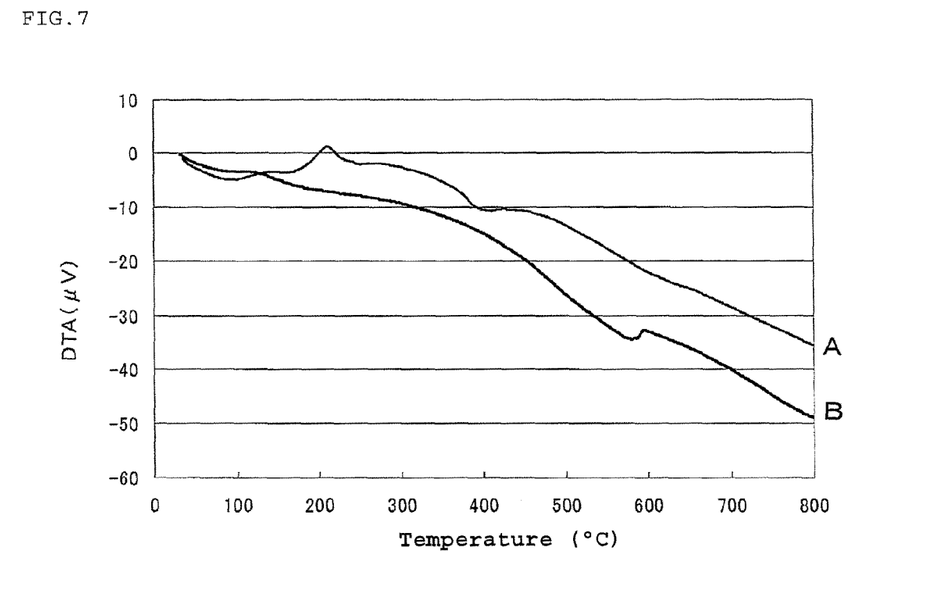
FIG. 7 shows a view illustrating results of measurement of DTA on the mixture of raw materials of Comparative Example, and the mixture of the raw materials of the present invention subjected to a heat treatment step 22.

FIG. 7 shows the results of the DTA measurement on Comparative Example. In FIG. 7, "A" indicates the results of the DTA measurement on a mixture obtained by mixing tin oxide $SnO_2$ and $H_3PO_4$ (manufactured by Wako Pure Chemical Industries, Ltd., a conc. phosphoric acid aqueous solution of 85% concentration) at a rate to give the molar ratio of Sn:P of 1:3. Whereas, "B" indicates the results of the DTA measurement on a mixture obtained by mixing powdery (about 1 μm) tin pyrophosphate (manufactured by Nippon Chemical Industrial Co., Ltd.) and $H_3PO_4$ (manufactured by Wako Pure Chemical Industries, Ltd., a conc. phosphoric acid aqueous solution of 85% concentration) at a rate to give the molar ratio of Sn:P of 1:0.5, and further subjecting the mixture to a heat treatment step at 400° C. for 1 hour thereafter.

From these results, it was revealed that the mixture of $SnO_2$ and $H_3PO_4$ gave a peak at around 200° C.; however, an endothermic reaction proceeded in the entire temperature range. Furthermore, it was revealed that the sample subjected only to the heat treatment step 22 without subjecting to the heat treatment step 21 also caused an endothermic reaction in the entire temperature range.

From the foregoing results, it was proven that even at the same temperature conditions, the reaction process when tin pyrophosphate and phosphoric acid were used as raw materials was completely different from the reaction process when tin oxide and phosphoric acid were used as raw materials. Moreover, the mixture prepared by using tin pyrophosphate and phosphoric acid as raw materials and subjecting to the heat treatment step 22 was also confirmed to go through different reaction processes.

Example 2

In order to study the upper limit of the temperature conditions applicable to the heat treatment step 22 in the method for manufacturing the proton-conducting structure of the present invention, the structure was manufactured in a similar procedure to Example 1 except that the preset temperature at the heat treatment step 22 in Example 1 was changed to 200° C., 300° C., or, 500° C., 600° C. The proton conductivity was measured on thus produced samples according to the aforementioned procedure. The proton conductivity at a measurement temperature of 100° C. or 200° C. on each sample is shown in Table 1 in combination with the results of Example 1.

TABLE 1

Relationship between preset temperature at heat treatment step 22 and proton conductivity (S/cm)

| Preset temperature at heat treatment step 22 | 200° C. (the present invention) | 300° C. (the present invention) | 400° C. (the present invention) | 500° C. (Comparative Example) | 600° C. (Comparative Example) |
|---|---|---|---|---|---|
| Proton conductivity (measured at 100° C.) | 0.120 | 0.096 | 0.130 | 0.006 | 0.002 |
| Proton conductivity (measured at 200° C.) | 0.191 | 0.159 | 0.264 | 0.015 | 0.002 |

From the foregoing results, it was ascertained that when the heat treatment step 22 was carried out at not less than 200° C. and not more than 400° C., the obtained structure exhibited favorable proton conductivity, and that when the preset temperature at the heat treatment step 22 is not lower than 500° C., the proton conductivity remarkably decreased.

In addition, with respect to the structure obtained by changing the temperature at the heat treatment step 22 to 300° C. or 600° C., the coordination number of O with respect to Sn was measured according to the aforementioned conversion particle yield process.

As a result, the sample obtained by setting the temperature at the heat treatment step 22 to 300° C. had the aforementioned coordination number of 7.0. From this result, formation of the coating layer 12 having a coordination number of O with respect to Sn of grater than 6 was confirmed, similarly to Example 1.

On the other hand, the sample obtained by setting the temperature at the heat treatment step 22 to 600° C. had the aforementioned coordination number of 5.5, which was comparative to the value of tin pyrophosphate (5.2). Accordingly, it was verified that the coating layer 12 in the present invention was not formed when the temperature at the heat treatment step 22 was a high temperature of 600° C.

Figure 8:
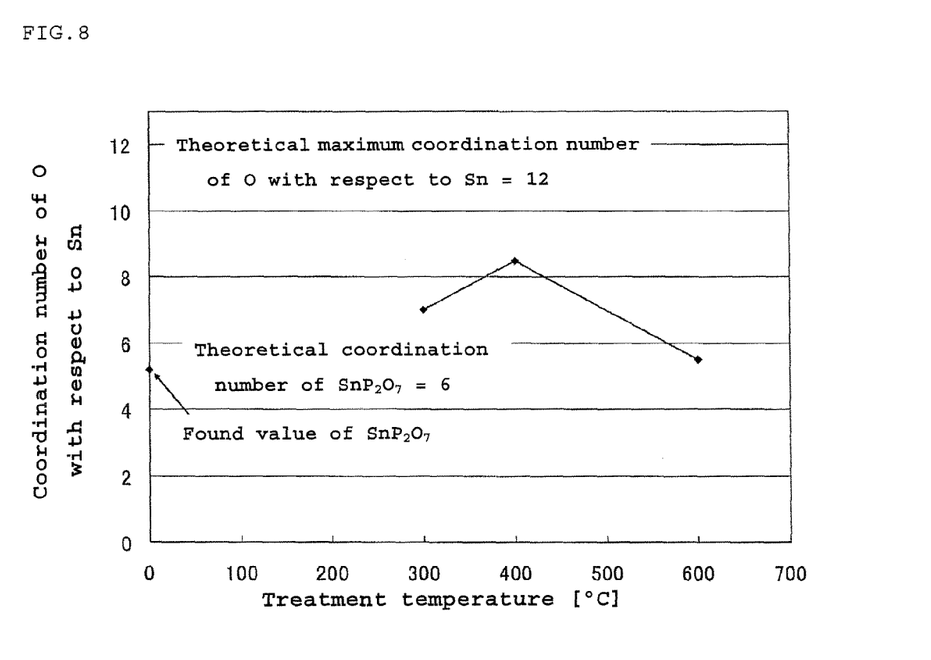
FIG. 8 shows a view illustrating a relationship between the preset temperature in the heat treatment step 22, and the coordination number of O with respect to Sn.

FIG. 8 shows the foregoing results in connection with the coordination number of O with respect to Sn in combination with the results of Example 1.

From the foregoing results, it was proven that a proton-conducting structure that exhibited favorable proton conductivity was manufactured by mixing tin pyrophosphate and phosphoric acid as raw materials, and carrying out the heat treatment step 21 of heating at a temperature of not less than 80° C. and not more than 150° C., followed by the heat treatment step 22 of heating at a temperature of not less than 200° C. and not more than 400° C. Additionally, it was confirmed that the proton-conducting structure had a structure containing tin pyrophosphate as the core 11, and the coating layer 12 formed on at least a part of the surface thereof, the coating layer 12 having a coordination number of O with respect to Sn of grater than 6.

Example 3

A structure was manufactured in a similar manner to Example 1 except that titanium pyrophosphate, silicon pyrophosphate, or zirconium pyrophosphate (all manufactured by Nippon Chemical Industrial Co., Ltd.) was used in place of tin pyrophosphate in Example 1. However, the weight of each pyrophosphate metal used was changed such that the molar ratio of metal in the pyrophosphate metal salt:P became 1:0.5. With regard to the obtained each structure, the proton conductivity was measured under the aforementioned conditions in the temperature range of from the room temperature to 250° C.

Figure 9:
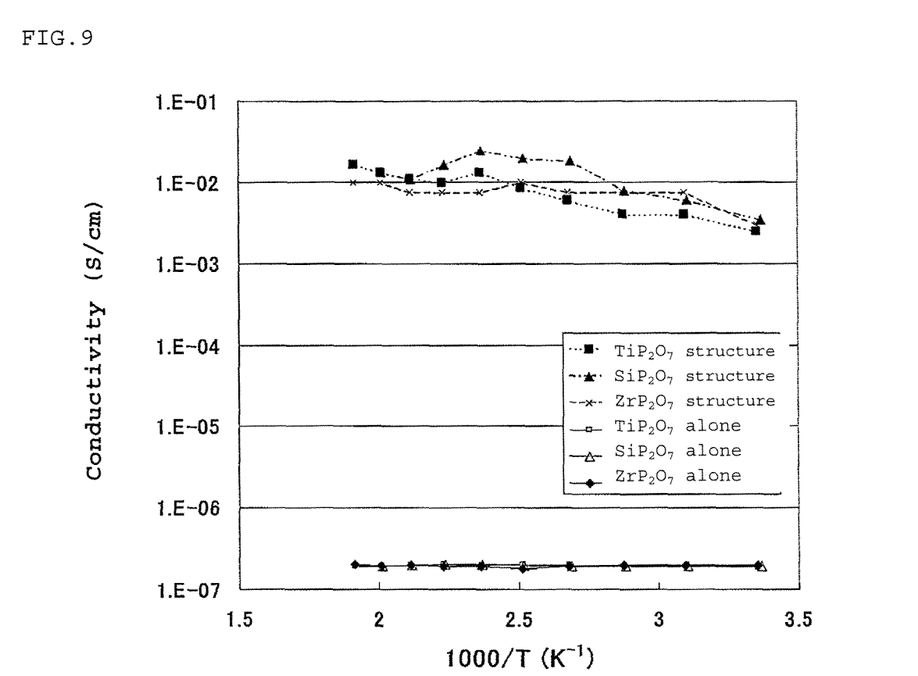
FIG. 9 shows a view illustrating results of measurement of proton conductivity in a proton-conducting structure obtained according to the manufacturing method of the present invention, and in a pyrophosphate metal salt.

FIG. 9 shows the results of the temperature dependency of the proton conductivity thus obtained. In FIG. 9, the measurement results on the manufactured structure are shown in combination with the measurement results on each single-phase pyrophosphate metal salt molded into a pellet form under the same conditions. From these results, it is demonstrated that each structure exhibited significantly higher proton conductivity as compared with each pyrophosphate metal salt. Accordingly, it was revealed that even when titanium pyrophosphate, silicon pyrophosphate, or zirconium pyrophosphate was used in place of tin pyrophosphate, a structure can be manufactured that achieves remarkably superior proton conductivity as compared with that achieved by each pyrophosphate metal salt in the temperature range of from the room temperature to 250° C.

From the foregoing results, the proton-conducting structure of the present invention, and the proton-conducting structure obtained by the manufacturing method of the present invention are most suitable as a solid electrolyte for use in fuel cells in an intermediate temperature range of not lower than 100° C.

Namely, when the solid electrolyte layer of the present invention is used in a fuel cell, more favorable specific conductance is attained, and thus improvement of the rate of electric power generation of fuel cells is expected.

[Industrial Applicability]

The proton-conducting structure according to the present invention, and the proton-conducting structure obtained by the manufacturing method of the present invention have superior proton conductivity, and are used for a solid electrolyte for use in fuel cells or hydrogen sensors.

[DESCRIPTION OF NUMERALS AND SIGNS]

| | |
|---|---|
| 11 | Core |
| 12 | Coating layer |
| 21 | First heat treatment step |
| 22 | Second heat treatment step |
| A | Results of DTA measurement on the mixture of tin oxide and phosphoric acid |
| B | Results of DTA measurement on the mixture containing tin pyrophosphate and phosphoric acid, which had been subjected to heat treatment step 22 |
| C | Proton conductivity exhibited by proton-conducting structure of Example 1 |
| D | Proton conductivity exhibited by tin pyrophosphate |

The invention claimed is:

1. A method for generating an electric power, the method comprising steps of:
    (a) preparing a fuel cell comprising:
        a cathode;
        an anode; and
        a solid electrolyte membrane; wherein
    at least one electrode selected from the cathode and the anode comprises a plurality of catalyst-holding particles coated with an electrolyte;
    the electrolyte comprises a core and a coating layer;
    the core is made of tin pyrophosphate;
    the coating layer is formed on at least a part of the surface of the core;
    the coating layer contains Sn and O; and
    the coordination number of O with respect to Sn is greater than 6 and less than 12; and
    (b) supplying oxygen and hydrogen to the cathode and the anode, respectively, to generate the electric power.

2. The method according to claim 1, wherein the step (b) is conducted at a temperature of not less than 100 Celsius degrees and not more than 200 Celsius degrees.

3. The method according to claim 1, wherein the cathode comprises the plurality of catalyst-holding particles coated with the electrolyte.

4. The method according to claim 1, wherein the anode comprises the plurality of catalyst-holding particles coated with the electrolyte.

* * * * *